(12) United States Patent
Takahashi et al.

(10) Patent No.: US 8,961,777 B2
(45) Date of Patent: Feb. 24, 2015

(54) METHOD FOR ACCURATELY QUANTIFYING A CHEMICAL SUBSTANCE CONTAINED IN A SAMPLE SOLUTION AT A SIGNIFICANTLY LOW CONCENTRATION OF NOT MORE THAN $1\times10^{-8}$M

(71) Applicant: Panasonic Corporation, Osaka (JP)

(72) Inventors: Makoto Takahashi, Osaka (JP); Satoshi Arimoto, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 132 days.

(21) Appl. No.: 13/905,841

(22) Filed: May 30, 2013

(65) Prior Publication Data

US 2013/0327657 A1 Dec. 12, 2013

(30) Foreign Application Priority Data

Jun. 6, 2012 (JP) ................................. 2012-128573

(51) Int. Cl.
*G01N 27/416* (2006.01)
*G01N 27/327* (2006.01)

(52) U.S. Cl.
CPC .......... *G01N 27/416* (2013.01); *G01N 27/3274* (2013.01)
USPC ........................................................ 205/792

(58) Field of Classification Search
CPC ............................ G01N 27/416; G01N 27/327
USPC ................. 204/403.01–403.15; 205/775, 792
See application file for complete search history.

(56) References Cited

U.S. PATENT DOCUMENTS

| 5,413,690 | A | 5/1995 | Kost et al. |
|---|---|---|---|
| 2009/0107582 | A1 | 4/2009 | Sayage |
| 2009/0117574 | A1 | 5/2009 | Labgold et al. |
| 2010/0203516 | A1 | 8/2010 | Campbell et al. |
| 2012/0216604 | A1 | 8/2012 | Arimoto |

FOREIGN PATENT DOCUMENTS

| EP | 569908 A2 | 11/1993 |
|---|---|---|
| EP | 569908 A3 | 11/1993 |
| EP | 569908 B1 | 11/1993 |
| JP | 59-224551 | 12/1984 |
| JP | 06-027081 A | 2/1994 |
| JP | 09-500727 A1 | 1/1997 |
| JP | 2006-250560 A | 9/2006 |
| JP | 2007-255906 A | 10/2007 |

(Continued)

*Primary Examiner* — Jennifer Dieterle
(74) *Attorney, Agent, or Firm* — McDermott Will & Emery LLP (57) ABSTRACT

Provided is a method for accurately quantifying a chemical substance contained in a sample solution at a significantly low concentration of not more than $1\times10^{-8}$M. First, prepared is a measurement system including a counter electrode 13, a first reference electrode 12, a first working electrode 11a, a second working electrode 11b and a second reference electrode 14. Second, voltages of V1 volts and V2 volts (V1>V2) are applied to the first working electrode 11a and the second working electrode 11b, respectively. Third, a voltage difference $\Delta E$ between the second working electrode 11b and the second reference electrode 14 is measured. Finally, the concentration of the chemical substance is calculated on the basis of the voltage difference $\Delta E$.

14 Claims, 4 Drawing Sheets

(56) References Cited

FOREIGN PATENT DOCUMENTS

| | | |
|---|---|---|
| JP | 2010517026 A | 5/2010 |
| JP | 2010-286423 A | 12/2010 |
| JP | 2010539515 A | 12/2010 |
| JP | 2011-058900 A | 3/2011 |
| JP | 2011-080773 A | 4/2011 |
| JP | 4991967 B1 | 8/2012 |
| WO | 2012114389 A1 | 8/2012 |

METHOD FOR ACCURATELY QUANTIFYING A CHEMICAL SUBSTANCE CONTAINED IN A SAMPLE SOLUTION AT A SIGNIFICANTLY LOW CONCENTRATION OF NOT MORE THAN $1\times10^{-8}$M

RELATED APPLICATIONS

This application claims the benefit of Japanese Application No. 2012-128573, filed on Jun. 6, 2012, the disclosure of which Application is incorporated by reference herein.

BACKGROUND OF THE INVENTION

1. Field of the Invention

The present invention relates to a method for accurately quantifying a chemical substance contained in a sample solution at a significantly low concentration of not more than $1\times10^{-8}$M.

2. Description of the Related Art

Japanese Patent Laid-Open Publication No. 2010-286423 discloses a method for quantifying a chemical substance contained in a sample solution by a potentiometric method. In the potentiometric method, a surface potential of a measurement electrode which varies with a chemical reaction is measured.

SUMMARY OF THE INVENTION

The purpose of the present invention is to provide a method for accurately quantifying a chemical substance contained in a sample solution at a significantly low concentration of not more than $1\times10^{-8}$M.

The present invention is a method for accurately quantifying a chemical substance contained in a sample solution at a significantly low concentration of not more than $1\times10^{-8}$M, the method comprising steps of:

(a) preparing a measurement system including a counter electrode, a first reference electrode, a first working electrode, a second working electrode and a second reference electrode;

(b) bringing the counter electrode, the first reference electrode, the first working electrode, the second working electrode and the second reference electrode into contact with the sample solution; wherein
the sample solution contains the chemical substance and an oxidation-reduction substance or contains the chemical substance modified with an oxidation-reduction substance;

(c) applying voltages of V1 volts and V2 volts (V1>V2) to the first working electrode and the second working electrode, respectively, for a first predetermined period t1 with use of a potentiostat so as to develop chemical reactions represented by the following chemical formulae (I) and (II) on the surfaces of the first working electrode 11a and the second working electrode 11b, respectively;

On the first working electrode:

(where, n represents an integer, and m represents a positive integer)

On the second working electrode:

(where, n represents an integer, and m represents a positive integer)

(d) stopping the application of the voltage to the second working electrode, when the first predetermined period t1 elapses;

(e) leaving the sample solution as it stands for a second predetermined period t2 after the step (d);

(f) measuring a voltage difference ΔE between the second working electrode and the second reference electrode after the step (e); and (g) calculating a concentration of the chemical substance on the basis of the following formula (III)

$$\Delta E = C1 \cdot \log_{10}(\text{the concentration of the chemical substance}) + C2 \quad \text{(III)}$$

C1: proportional constant

C2: constant

In one embodiment, the voltage difference between the voltages of V1 and V2 in the step (c) is not less than 0.3 volts and not more than 0.6 volts.

In one embodiment, the first predetermined period t1 is not less than 10 seconds and not more than 600 seconds.

In one embodiment, the second predetermined period t2 is not less than 10 seconds and not more than 600 seconds.

In one embodiment, the oxidation-reduction substance is a ferrocene derivative.

In one embodiment, the ferrocene derivative is ferrocenecarboxylic acid.

In one embodiment, the chemical substance is an antibody.

The another present invention is a method for accurately quantifying a chemical substance contained in a sample solution at a significantly low concentration of not more than $1\times10^{-8}$M, the method comprising steps of:

(a) preparing a measurement system including a counter electrode, a first reference electrode, a first working electrode, a second working electrode and a second reference electrode;

(b) bringing the counter electrode, the first reference electrode, the first working electrode and the second working electrode into contact with the sample solution; wherein
the sample solution contains the chemical substance and an oxidation-reduction substance or contains the chemical substance modified with an oxidation-reduction substance; and
the second reference electrode is not in contact with the sample solution;

(c) applying voltages of V1 volts and V2 volts (V1>V2) to the first working electrode and the second working electrode, respectively, for a first predetermined period t1 with use of a potentiostat so as to develop chemical reactions represented by the following chemical formulae (I) and (II) on the surfaces of the first working electrode and the second working electrode, respectively;

On the first working electrode:

(I)

(where, n represents an integer, and m represents a positive integer)

On the second working electrode:

(II)

(where, n represents an integer, and m represents a positive integer)

(d) stopping the application of the voltage to the second working electrode when the first predetermined period t1 elapses;

(e) leaving the sample solution as it stands for a second predetermined period t2 after the step (d);

(f) bringing the second reference electrode into contact with the sample solution;

(g) measuring a voltage difference ΔE between the second working electrode and the second reference electrode after the step (f); and (h) calculating a concentration of the chemical substance on the basis of the following formula (III)

$$\Delta E = C1 \cdot \log_{10}(\text{the concentration of the chemical substance}) + C2 \quad \text{(III)}$$

C1: proportional constant
C2: constant

In one embodiment, the voltage difference between the voltages of V1 and V2 in the step (c) is not less than 0.3 volts and not more than 0.6 volts.

In one embodiment, the first predetermined period t1 is not less than 10 seconds and not more than 600 seconds.

In one embodiment, the second predetermined period t2 is not less than 10 seconds and not more than 600 seconds.

In one embodiment, the oxidation-reduction substance is ferrocene derivative.

In one embodiment, the ferrocene derivative is ferrocenecarboxylic acid.

In one embodiment, the chemical substance is an antibody.

The present invention provides a method for accurately quantifying a chemical substance contained in a sample solution at a significantly low concentration of not more than $1 \times 10^{-8}$M.

Other features, elements, processes, steps, characteristics and advantages of the present invention will become more apparent from the following detailed description of preferred embodiments of the present invention with reference to the attached drawings.

DETAILED DESCRIPTION OF THE INVENTION

The embodiments of the present invention are described below.

Embodiment 1

Step (a)

Figure 1A:
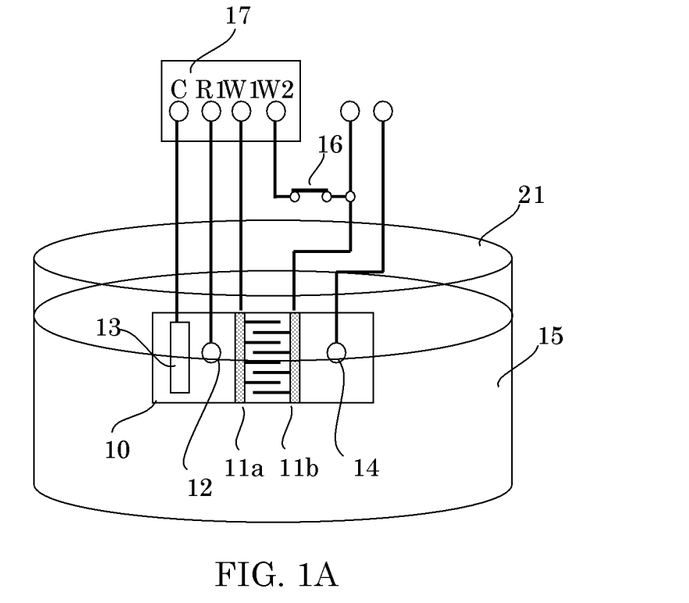
FIG. 1A schematically shows the step (a)-step (c) in the embodiment 1.

FIG. 1A shows a measurement system used in the embodiment 1. The measurement system includes a counter electrode 13, a first reference electrode 12, a first working electrode 11a, a second working electrode 11b and a second reference electrode 14. The counter electrode 13, the first reference electrode 12, the first working electrode 11a and the second working electrode 11b are connected to a potentiostat 17. A switch 16 is provided between the potentiostat 17 and the second working electrode 11b. In the step (b) and the step (c), the switch 16 is kept on.

It is desirable that the first working electrode 11a and the second working electrode 11b are comb-shaped electrodes. It is desirable that these two comb-shaped electrodes are engaged alternately.

An example of the counter electrode 13 is a palladium electrode. An example of the first reference electrode 12 is a silver/silver chloride electrode.

An example of the first working electrode 11a is a gold electrode. An example of the second working electrode 11b is also a gold electrode. It is desirable that the gold electrode is covered with a self-assembled film consisting of alkanethiol. It is desirable that the first working electrode 11a and the second working electrode 11b are composed of a pair of identical electrodes.

Step (b)

Figure 1B:
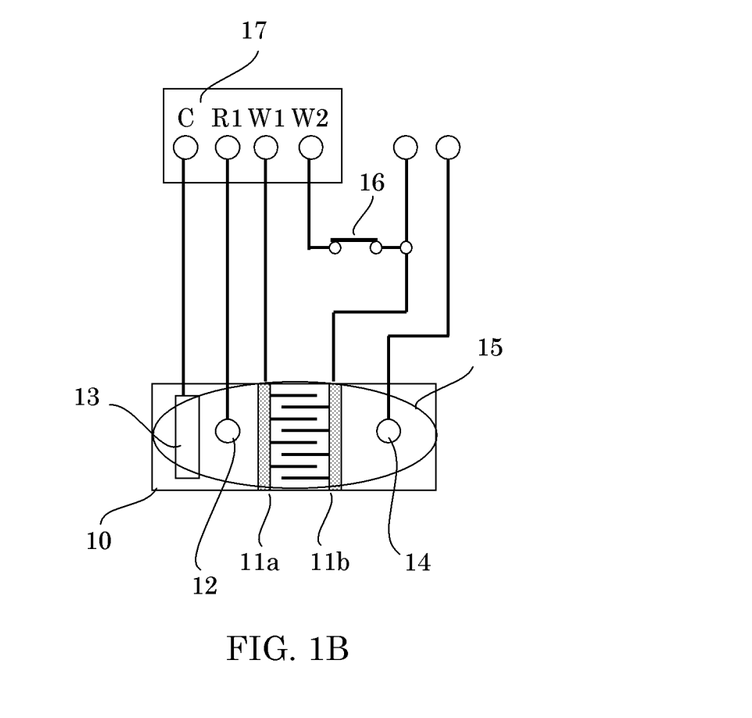
FIG. 1B schematically shows the step (a)-step (c) in the embodiment 1.

The step (b) is performed after the step (a). In the step (b), the counter electrode 13, the first reference electrode 12, the first working electrode 11a, the second working electrode 11b and the second reference electrode 14 are brought into contact with the sample solution 15. More particularly, as shown in FIG. 1B, the sample solution 15 is dropped onto a substrate 10 in such a manner that the sample solution covers the counter electrode 13, the first reference electrode 12, the first working electrode 11a, the second working electrode 11b and the second reference electrode 14. Instead of this, as shown in FIG. 1A, the counter electrode 13, the first reference electrode 12, the first working electrode 11a, the second working electrode 11b and the second reference electrode 14 are immersed in the sample solution 15 contained in a vessel 21. It is desirable that the sample solution 15 is an aqueous solution. It is more desirable that the sample solution 15 is a buffer solution.

In FIG. 1A and FIG. 1B, the counter electrode 13, the first reference electrode 12, the first working electrode 11a, the second working electrode 11b and the second reference electrode 14 are formed on one insulating substrate 10. Accordingly, the sample solution 15 is dropped onto the substrate 10, or the substrate 10 is immersed in the sample solution 15. However, these five electrodes 11-14 may be brought into contact with the sample solution 15 separately without use of the substrate 10.

Here, the chemical substance to be quantified according to the present embodiment is described. The sample solution 15 contains the chemical substance and an oxidation-reduction substance. Instead of this, the sample solution 15 contains the chemical substance modified with the oxidation-reduction substance. The sample solution 15 contains an antibody modified with ferrocenecarboxylic acid in the example, which is described later.

The oxidation-reduction substance is contained in the sample solution 15 in a state of either oxidant or reductant. The oxidation-reduction substance is changed from the oxidant state to the reductant state or from the reductant state to the oxidant state, when the chemical substance is changed to another chemical substance by the chemical reaction associated with exchange of electrons, namely, the oxidant-reduction reaction.

An example of the chemical substance is a sugar and an antibody. An example of the oxidation-reduction substance is flavin adenine dinucleotide (hereinafter, referred to as "FAD"), potassium ferrocyanide (reductant), potassium ferricyanide (oxidant), ferrocene (and derivatives thereof) or quinone (and the derivative thereof). Generally, the oxidation-reduction substance is called "electron mediator".

Figure 4:
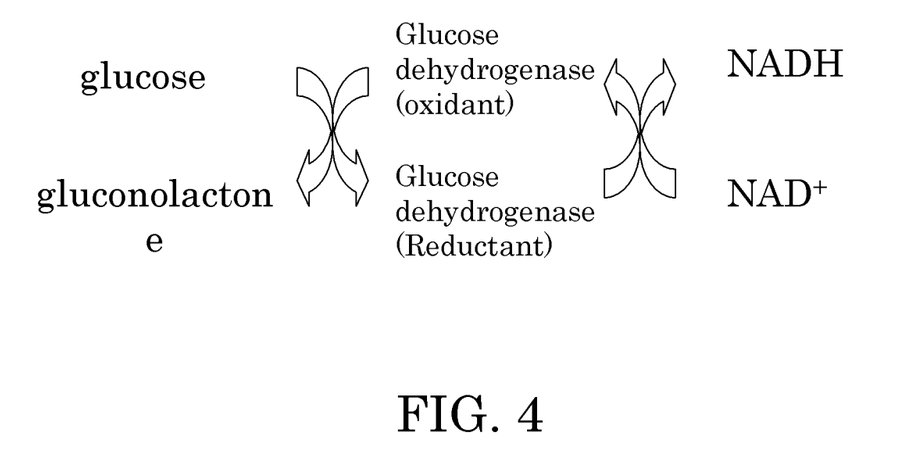
FIG. 4 shows oxidation of glucose by glucose dehydrogenase.

As one example, oxidation of glucose by glucose dehydrogenase is described. As shown in FIG. 4, glucose and nicotinamide adenine dinucleotide are used as the chemical substance and the oxidation-reduction substance, respectively. Glucose is changed to gluconolactone by the glucose dehydrogenase. At the same time, the nicotinamide adenine dinucleotide oxidant (hereinafter, referred to as "NAD+") is changed to the reductant thereof (hereinafter, referred to as "NADH").

Step (c)

The step (c) is performed after the step (b). In the step (c), the voltages of V1 volts and V2 volts (V1>V2) are applied to the first working electrode 11a and the second working electrode 11b, respectively, for a first predetermined period t1 with use of the potentiostat 17. This voltage application develops the chemical reaction represented by the following chemical formula (I) on the surface of the first working electrode 11a.

(where, n represents an integer, and m represents a positive integer)

At the same time, the voltage application develops the chemical reaction represented by the following chemical formula (II) on the surface of the second working electrode 11b.

(where, n represents an integer, and m represents a positive integer)

In the step (c), the first working electrode 11a and the second working electrode 11b serve as an anode electrode and a cathode electrode, respectively.

It is desirable that the voltage V1 is not less than 0.3 volts and not more than 0.6 volts. In case where the voltage V1 is less than 0.3 volts, the chemical reaction represented by the chemical formula (I) may not be developed enough. In case where the voltage V1 is more than 0.6 volts, an electrolysis reaction of water may be developed.

It is desirable that the voltage V2 is not less than −0.2 volts and not more than 0 volts. In case where the voltage V2 is less than −0.2 volts, an electrolysis reaction of water may be developed. In case where the voltage V2 is more than 0 volts, the chemical reaction represented by the chemical formula (II) may not be developed well.

It is desirable that the voltage difference (V1−V2) is not less than 0.2 volts and not more than 0.8 volts. In case where the voltage difference (V1−V2) is less than 0.2 volts, an oxidation-reduction reaction cycle may not be developed sufficiently. In case where the voltage difference (V1−V2) is more than 0.8 volts, an electrolysis reaction of water may be developed.

As one example, the voltages V1 and V2 are 0.3 volts (vs. the first reference electrode 12) and 0 volts (vs. the first reference electrode 12), respectively.

It is desirable that the first predetermined period t1 is not less than 10 seconds and not more than 600 seconds. In case where the first predetermined period t1 is less than 10 seconds, the chemical reactions represented by the chemical formula (I) and (II) may not be developed sufficiently. In case where the first predetermined period t1 is more than 600 seconds, the solvent (water) contained in the sample solution 15 may be evaporated to vary the concentration of the sample solution 15. It is desirable that the second reference electrode 14 is in a floating state in the step (c).

Step (d)

When the first predetermined period t1 elapses, the application of voltage V2 to the second working electrode 11b is stopped. More particularly, the switch 16 is turned off. By turning off the switch 16, the electrical state of the second working electrode 11b becomes a floating state. It is desirable that the voltage V1 is maintained at the first working electrode 11a in the step (d).

Step (e)

After the step (d), the step (e) is performed. In the step (e), the sample solution 15 is left as it stands for a predetermined period t2.

It is desirable that the second predetermined period t2 is not less than 10 seconds and not more than 600 seconds. In case where the second predetermined period t2 is less than 10 seconds, the noise generated by switching in the step (d) may be included erroneously in the voltage difference ΔE, which is described later. In case where the second predetermined period t2 is more than 600 seconds, the solvent (water) contained in the sample solution 15 may be evaporated to vary the concentration of the sample solution 15.

Step (f)

Figure 2A:
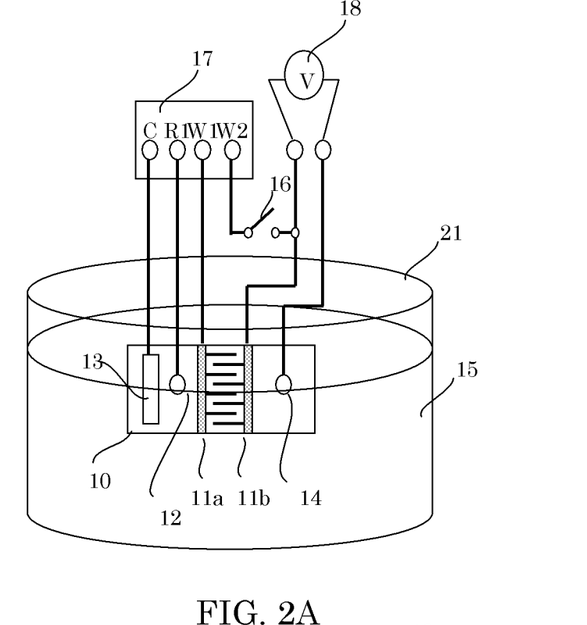
FIG. 2A schematically shows the step (f) in the embodiment 1.
Figure 2B:
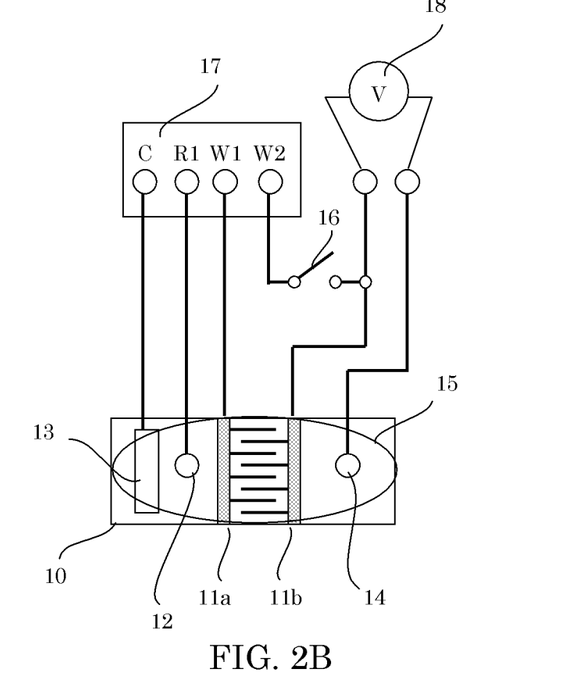
FIG. 2B schematically shows the step (f) in the embodiment 1.

When the second predetermined period t2 elapses, the voltage difference ΔE between the second working electrode 11b and the second reference electrode 14 is measured. More particularly, as shown in FIG. 2A and FIG. 2B, a voltmeter 18 is interposed electrically between the second working electrode 11b and the second reference electrode 14. Needless to say, in the step (f), the second working electrode 11b and the second reference electrode 14 are in contact with the sample solution 15.

The present inventors have discovered that the voltage difference ΔE is proportional to the concentration of the chemical substance contained in the sample solution 15, even when the chemical substance contained in the sample solution 15 has a significantly low concentration of less than $1 \times 10^{-8}$M. The present invention is characterized by this discovery.

Here, the present inventors will describe the theory that the voltage difference ΔE is proportional to the concentration of the chemical substance contained in the sample solution 15.

In the step (c), the oxidation-reduction substance (oxidant) is generated on the surface of the first working electrode 11a. The amount of the oxidation-reduction substance (oxidant) generated on the surface of the first working electrode 11a is proportional to the amount of the chemical substance to be quantified.

Subsequently, while the sample solution 15 is left as it stands in the step (e), the oxidation-reduction substance (oxidant) is diffused from the surface of the first working electrode 11a. As a result, a part of the diffused oxidation-reduction substance (oxidant) reaches the surface of the second working electrode 11b. The oxidation-reduction substance (oxidant) which has reaches the surface of the second working electrode 11b generates a voltage difference between the second working electrode 11b and the second reference electrode 14. This voltage difference is measured as the voltage difference ΔE.

Since the amount of the oxidation-reduction substance (oxidant) generated on the surface of the first working electrode 11a is proportional to the amount of the chemical substance to be quantified, the voltage difference ΔE is also proportional to the amount of the chemical substance to be quantified.

However, the present inventors do not want to be bound by the above-mentioned theory.

Step (g)

Finally, on the basis of the voltage difference ΔE measured in the step (f), the concentration of the chemical substance is calculated in accordance with the following formula (III):

$$\Delta E = C1 \cdot \log_{10}(\text{the concentration of the chemical substance}) + C2 \quad \text{(III)}$$

C1: proportional constant
C2: constant

Needless to say, when the concentration of the chemical substance is calculated on the basis of the voltage difference ΔE measured in the step (f), a calibration curve is used.

In other words, a plurality of the voltage differences ΔE are measured using a plurality of the sample solutions each containing the chemical substance at a different known concentration. On the basis of the plurality of the measured voltage differences ΔE and the concentrations of the chemical substance, a calibration curve is prepared. The calibration curve has a predetermined proportional constant C1 and a predetermined constant C2.

Next, using a sample solution containing the chemical substance at an unknown concentration, the voltage difference ΔE is measured. Using the calibration curve, the concentration of the chemical substance is calculated from the measured voltage difference ΔE.

The formula (III) is equivalent to the following formula (IV):

$$(\text{the concentration of the chemical substance}) = 10^{\{(\Delta E - d)/e\}} \quad \text{(IV)}$$

where d and e are constants.

Embodiment 2

The embodiment 2 is identical to the embodiment 1, except for the following items (A) and (B).

(A): In the step (b), the counter electrode 13, the first reference electrode 12, the first working electrode 11a and the second working electrode 11b are brought into contact with the sample solution 15. The second reference electrode 14 is not brought into contact with the sample solution 15.

(B): Before the step (f), the second reference electrode 14 is brought into contact with the sample solution 15.

In the embodiment 2, the substrate 10 may not used. The individual five electrodes 11-14 may be brought into contact with the sample solution 15 separately. Alternatively, the substrate 10 may comprise the counter electrode 13, the first reference electrode 12, the first working electrode 11a and the second working electrode 11b. This substrate 10 does not comprise the second reference electrode 14.

Example

The following examples describe the present invention in more detail.

The example is composed of the example 1a, the example 1b, the example 1c and the example 1d.

Example 1a

The electrochemical measurement system shown in FIG. 1B was prepared. This measurement system comprised the substrate 10, the switch 16, the potentiostat 17 and a pH meter (not shown). The substrate 10 comprised the first working electrode 11a, the second working electrode 11b, the first reference electrode 12, the counter electrode 13 and the second reference electrode 14. The potentiostat 17 was available from BAS Inc. under the trade name of "dual potentiostat ALS-832C". The pH meter was available from HORIBA Ltd. under the trade name of "F-72T".

The first working electrode 11a and the second working electrode 11b were comb-shaped electrodes each formed of gold covered with a self-assembled film composed of alkanethiol. These two comb-shaped electrodes were engaged alternately. The comb-shaped electrode had an electrode width of 2 micrometers. The interval between the comb-shaped electrodes, namely, the electrode interval, was 2 micrometers.

The first reference electrode 12 was a silver/silver chloride electrode. The counter electrode 13 was a palladium electrode. The second reference electrode 14 was a silver/silver chloride electrode, similarly to the first reference electrode 12.

Then, the sample solution 15 was dropped onto the substrate 10. In this way, as shown in FIG. 1B, the substrate 10 was covered with the sample solution 15.

The sample solution 15 contained chemical reagents shown in the following Table 1.

TABLE 1

| Chemical reagents | Concentration |
| --- | --- |
| NaCl | 7.0 mM |
| KCl | 2.7 mM |
| $Na_2HPO_4$ | 10.0 mM |
| $KH_2PO_4$ | 1.8 mM |
| Human serum albumin | 10.0 mg/ml |
| Ferrocene-labeled anti-human serum albumin antibody | $10^{-8}$ M |

The switch 16 was turned on to apply the voltages V1 of 0.3 volts and V2 of 0 volts (vs. Ag/AgCl) to the first working electrode 11a and the second working electrode 11b, respectively, for 60 seconds.

In this way, the chemical reaction represented by the following Chem 1 was developed on the first working electrode 11a.

[Chem 1]

The chemical reaction represented by the following Chem 2 was developed on the second working electrode 11b.

[Chem 2]

Then, the switch 16 was turned off.

The sample solution 15 was left as it stood for 180 seconds. When the 180 seconds had elapsed, as shown in FIG. 2B, the voltage difference ΔE between the second working electrode 11b and the second reference electrode 14 was measured with the voltmeter 18. The results are shown in Table 2 as the voltage difference ΔE measured for the first time. Meanwhile, the voltage of the first working electrode 11a was maintained at 0.3 volts.

The example 1a was repeated and the voltage difference ΔE was measured again. The results are shown in Table 2 as the voltage difference ΔE measured for the second time.

Example 1b

The experiment similar to the example 1a was performed, except that the concentration of the ferrocene-labeled anti-human serum albumin antibody was $1 \times 10^{-9}$ M.

Example 1c

The experiment similar to the example 1a was performed, except that the concentration of the ferrocene-labeled anti-human serum albumin antibody was $1 \times 10^{-10}$ M.

Example 1d

The experiment similar to the example 1a was performed, except that the concentration of the ferrocene-labeled anti-human serum albumin antibody was $1 \times 10^{-11}$ M.

TABLE 2

| | Concentration of the ferrocene-labeled anti-human serum albumin antibody | Voltage difference ΔE measured for the first time | Voltage difference ΔE measured for the second time | Average of Voltage difference ΔE |
| --- | --- | --- | --- | --- |
| Example 1a | $10^{-8}$ M | 26.3 mV | 26.3 mV | 26.3 mV |
| Example 1b | $10^{-9}$ M | 23.4 mV | 21.3 mV | 22.4 mV |
| Example 1c | $10^{-10}$ M | 11.7 mV | 16.5 mV | 14.1 mV |
| Example 1d | $10^{-11}$ M | 7.2 mV | 13.9 mV | 10.6 mV |

Figure 3:
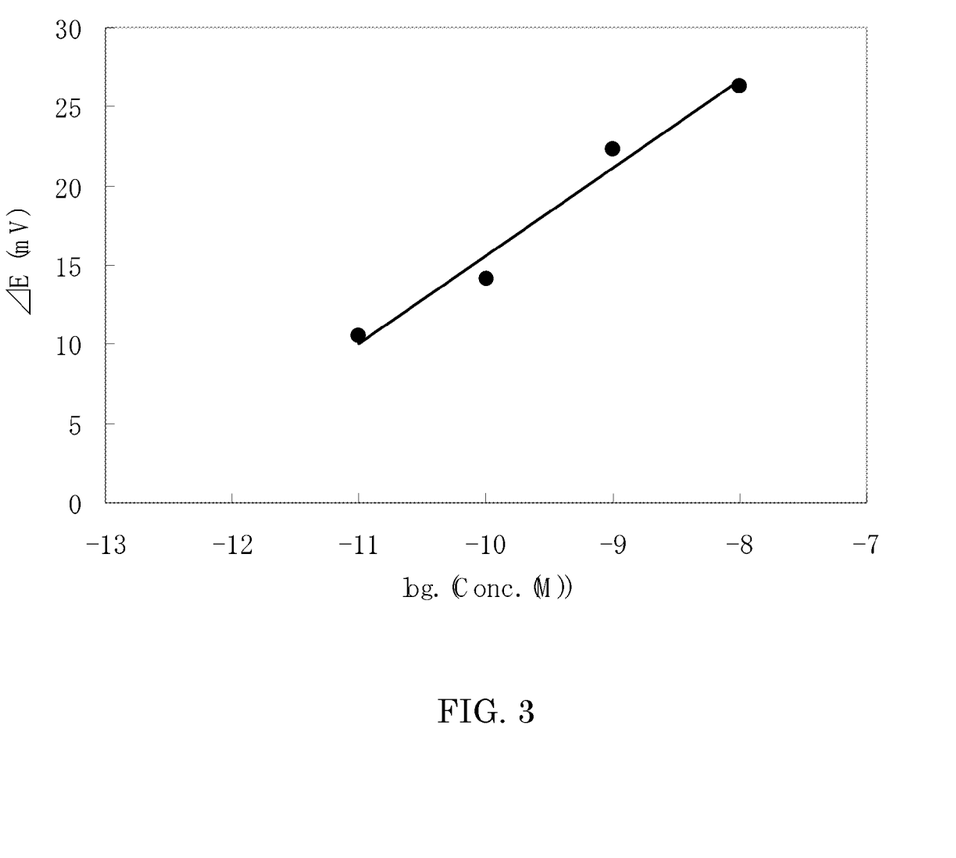
FIG. 3 is a graph showing the result of the example 1.

FIG. 3 is a graph showing the relationship between the average of the voltage difference ΔE and the concentration of the ferrocene-labeled anti-human serum albumin antibody. As is clear from FIG. 3, the average of the voltage difference ΔE is proportional to the common logarithm of the concentration of the ferrocene-labeled anti-human serum albumin antibody. In the example 1, the following formula was satisfied.

Average of the voltage difference $\Delta E = 5.55 \cdot \log_{10}$(the concentration of the antibody)$+71.05$ Accordingly, the graph shown in FIG. 3 can be served as a calibration curve. Using this calibration curve, the chemical substance contained in the sample solution at a significantly low concentration of not more than $1 \times 10^{-8}$ M is quantified accurately using the oxidation-reduction substance (e.g., ferrocene derivative). In other words, the concentration of the chemical substance is measured accurately with use of the method according to the present invention, when the chemical substance is predicted to be contained in the sample solution at a significantly low concentration of not more than $1 \times 10^{-8}$ M, however, the accurate concentration is unknown.

If the method according to the present invention has not been discovered, it would be difficult for a skilled person to measure accurately the concentration of the chemical substance contained in the sample solution at a significantly low concentration of not more than $1 \times 10^{-8}$ M.

The present invention provides a method for accurately quantifying the chemical substance contained in the sample solution at a significantly low concentration of not more than $1 \times 10^{-8}$ M.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

The invention claimed is:

1. A method for accurately quantifying a chemical substance contained in a sample solution at a significantly low concentration of not more than $1 \times 10^{-8}$M, the method comprising steps of:
   (a) preparing a measurement system including a counter electrode, a first reference electrode, a first working electrode, a second working electrode and a second reference electrode;
   (b) bringing the counter electrode, the first reference electrode, the first working electrode, the second working electrode and the second reference electrode into contact with the sample solution; wherein
   the sample solution contains the chemical substance and an oxidation-reduction substance or contains the chemical substance modified with an oxidation-reduction substance;
   (c) applying voltages of V1 volts and V2 volts (V1>V2) to the first working electrode and the second working electrode, respectively, for a first predetermined period t1 with use of a potentiostat so as to develop chemical reactions represented by the following chemical formulae (I) and (II) on the surfaces of the first working electrode and the second working electrode, respectively;
   On the first working electrode:

(reductant) (oxidant) (I)

(where, n represents an integer, and m represents a positive integer)
On the second working electrode:

(oxidant) (reductant) (II)

(where, n represents an integer, and m represents a positive integer)
   (d) stopping the application of the voltage to the second working electrode, when the first predetermined period t1 elapses;
   (e) leaving the sample solution as it stands for a second predetermined period t2 after the step (d);
   (f) measuring a voltage difference ΔE between the second working electrode and the second reference electrode after the step (e); and
   (g) calculating a concentration of the chemical substance on the basis of the following formula (III)

$$\Delta E = C1 \cdot \log_{10}(\text{the concentration of the chemical substance}) + C2 \quad \text{(III)}$$

C1: proportional constant
C2: constant.

2. The method according to claim 1, wherein
the voltage difference between the voltages of V1 and V2 in the step (c) is not less than 0.3 volts and not more than 0.6 volts.

3. The method according to claim 1, wherein
the first predetermined period t1 is not less than 10 seconds and not more than 600 seconds.

4. The method according to claim 1, wherein
the second predetermined period t2 is not less than 10 seconds and not more than 600 seconds.

5. The method according to claim 1, wherein
the oxidation-reduction substance is a ferrocene derivative.

6. The method according to claim 5, wherein
the ferrocene derivative is ferrocenecarboxylic acid.

7. The method according to claim 1, wherein
the chemical substance is an antibody.

8. A method for accurately quantifying a chemical substance contained in a sample solution at a significantly low concentration of not more than $1 \times 10^{-8}$M, the method comprising steps of:
   (a) preparing a measurement system including a counter electrode, a first reference electrode, a first working electrode, a second working electrode and a second reference electrode;
   (b) bringing the counter electrode, the first reference electrode, the first working electrode and the second working electrode into contact with the sample solution; wherein
   the sample solution contains the chemical substance and an oxidation-reduction substance or contains the chemical substance modified with an oxidation-reduction substance; and
   the second reference electrode is not in contact with the sample solution;
   (c) applying voltages of V1 volts and V2 volts (V1>V2) to the first working electrode and the second working electrode, respectively, for a first predetermined period t1 with use of a potentiostat so as to develop chemical reactions represented by the following chemical formulae (I) and (II) on the surfaces of the first working electrode and the second working electrode, respectively;
   On the first working electrode:

(reductant) (oxidant) (I)

(where, n represents an integer, and m represents a positive integer)
On the second working electrode:

(oxidant) (reductant) (II)

(where, n represents an integer, and m represents a positive integer)

(d) stopping the application of the voltage to the second working electrode when the first predetermined period t1 elapses;

(e) leaving the sample solution as it stands for a second predetermined period t2 after the step (d);

(f) bringing the second reference electrode into contact with the sample solution;

(g) measuring a voltage difference ΔE between the second working electrode and the second reference electrode after the step (f); and (h) calculating a concentration of the chemical substance on the basis of the following formula (III)

$$\Delta E = C1 \cdot \log_{10}(\text{the concentration of the chemical substance}) + C2 \quad \text{(III)}$$

C1: proportional constant
C2: constant.

9. The method according to claim 8, wherein
the voltage difference between the voltages of V1 and V2 in the step (c) is not less than 0.3 volts and not more than 0.6 volts.

10. The method according to claim 8, wherein
the first predetermined period t1 is not less than 10 seconds and not more than 600 seconds.

11. The method according to claim 8, wherein
the second predetermined period t2 is not less than 10 seconds and not more than 600 seconds.

12. The method according to claim 8, wherein
the oxidation-reduction substance is a ferrocene derivative.

13. The method according to claim 12, wherein
the ferrocene derivative is ferrocenecarboxylic acid.

14. The method according to claim 8, wherein
the chemical substance is an antibody.

* * * * *